US011767393B2

(12) United States Patent
Dhawan et al.

(10) Patent No.: US 11,767,393 B2
(45) Date of Patent: Sep. 26, 2023

(54) (HYDROXYALKYL)AMINOPHENOL POLYMERS AND METHODS OF USE

(71) Applicant: Ecolab USA Inc., St. Paul, MN (US)

(72) Inventors: Ashish Dhawan, Aurora, IL (US); Carter M. Silvernail, Lakeville, MN (US)

(73) Assignee: Ecolab USA Inc., St. Paul, MN (US)

(*) Notice: Subject to any disclaimer, the term of this patent is extended or adjusted under 35 U.S.C. 154(b) by 0 days.

(21) Appl. No.: 17/506,951

(22) Filed: Oct. 21, 2021

(65) Prior Publication Data

US 2022/0119574 A1 Apr. 21, 2022

Related U.S. Application Data

(60) Provisional application No. 63/094,597, filed on Oct. 21, 2020.

(51) Int. Cl.
C08G 8/36 (2006.01)
C02F 1/40 (2023.01)
C08G 8/16 (2006.01)
C08G 8/10 (2006.01)
C08G 8/22 (2006.01)
C10G 29/22 (2006.01)

(52) U.S. Cl.
CPC .......... C08G 8/36 (2013.01); C02F 1/40 (2013.01); C08G 8/10 (2013.01); C08G 8/16 (2013.01); C08G 8/22 (2013.01); C10G 29/22 (2013.01); C08G 2261/1422 (2013.01); C08G 2261/1424 (2013.01); C08G 2261/31 (2013.01); C10G 2300/206 (2013.01)

(58) Field of Classification Search
CPC ... C08G 8/36; C08G 8/10; C08G 8/16; C08G 8/22; C08G 2261/1422; C08G 2261/1424; C08G 2261/31; C02F 1/40; C10G 29/22; C10G 2300/206
See application file for complete search history.

(56) References Cited

U.S. PATENT DOCUMENTS

| 2,518,577 A | 8/1950 | Thompson et al. |
| 2,797,152 A | 6/1957 | Hughes et al. |
| 2,864,797 A | 12/1958 | De Groote et al. |
| 2,907,801 A | 10/1959 | Johnson et al. |
| 3,010,912 A | 11/1961 | Hardman |
| 3,678,113 A | 7/1972 | Klopfer |
| 3,696,050 A | 10/1972 | Werts, III et al. |
| 3,697,275 A | 10/1972 | Hayakawa et al. |
| 3,959,358 A | 5/1976 | Jursich |
| 4,003,800 A | 1/1977 | Bacha et al. |
| 4,038,434 A | 7/1977 | Young |
| 4,117,238 A | 9/1978 | Ackermann et al. |
| 4,337,103 A | 6/1982 | Elrick et al. |
| 4,374,742 A | 2/1983 | Evans et al. |
| 4,585,796 A | 4/1986 | Alig et al. |
| 4,654,451 A | 3/1987 | Miller et al. |
| 4,675,444 A | 6/1987 | Matsunaga et al. |
| 4,692,544 A | 9/1987 | Goemer et al. |
| 4,744,881 A | 5/1988 | Reid |
| 5,103,032 A | 4/1992 | Turner et al. |
| 5,213,699 A | 5/1993 | Babiarz et al. |
| 5,219,480 A | 6/1993 | Gutierrez et al. |
| 5,266,442 A | 11/1993 | Ooms |
| 5,320,765 A | 6/1994 | Fetterman, Jr. et al. |
| 5,340,369 A | 8/1994 | Koch et al. |
| 5,443,596 A | 8/1995 | Junino et al. |
| 5,476,973 A | 12/1995 | Hatano et al. |
| 5,583,247 A | 12/1996 | Nesvadba et al. |
| 5,728,872 A | 3/1998 | Riemenschneider |
| 5,763,144 A | 6/1998 | Jeganathan |
| 5,909,337 A | 6/1999 | Tyndall, III |
| 6,024,769 A | 2/2000 | Cotteret |
| 6,040,482 A | 3/2000 | Harris et al. |
| 6,452,020 B1 | 9/2002 | Batlaw et al. |
| 6,639,026 B2 | 10/2003 | Eldin |
| 7,045,647 B2 | 5/2006 | Benage |
| 7,204,858 B2 | 4/2007 | Desenne et al. |
| 7,498,467 B2 | 3/2009 | Shiraki |
| 7,569,615 B2 | 8/2009 | Leinweber et al. |
| 7,671,098 B2 | 3/2010 | Leinweber et al. |
| 7,900,590 B2 | 3/2011 | Cleveland et al. |
| 7,902,317 B2 | 3/2011 | Kumar et al. |
| 8,530,397 B2 | 9/2013 | Bera et al. |
| 9,168,217 B2 | 10/2015 | Schweinsberg |
| 9,212,330 B2 | 12/2015 | Bolton et al. |

(Continued)

FOREIGN PATENT DOCUMENTS

CA 467388 A 8/1950
DE 343151 C 10/1921

(Continued)

OTHER PUBLICATIONS

Kluchesky et al. "Polymerization Inhibition and Stopping Agents", Ind. Eng. Chem., 41: pp. 1768-1771 (1949).

Voronkov et al. "XRN=2846043" Journal of General Chemistry of the USSR, vol. 48, 2 pages, abstract (1978).

Ladona et al. "Biotransformation and Clearance of 3-(Phenylamino)propane-1,2-diol, a Compound Present in Samples Related to Toxic Oil Syndrome, in C57BL/6 and A/J Mice", Chem. Res. Toxicol., 12: pp. 1127-1137 (1999).

Zeinalova et al. "Inhibition of the oxidation of synthetic oils at high temperatures", Chemistry and Technology of Fuels and Oils, 13: pp. 40-42 (1977).

(Continued)

Primary Examiner — Shane Fang
(74) Attorney, Agent, or Firm — Kagan Binder, PLLC

(57) ABSTRACT

Polymers are formed by the condensation of bis(hydroxycarbyl)-aminophenolic compounds with aldehydes. The condensation polymers include one or more repeat units having bis(hydroxycarbyl)amino functionality. The polymers are useful as antifoulants, antipolymerants, rheology modifiers, dehazers, polymerization retardants, surfactants, or a combination of these in one or more industrial process streams.

21 Claims, No Drawings

(56) References Cited

U.S. PATENT DOCUMENTS

| | | |
|---|---|---|
| 9,266,797 B2 | 2/2016 | Colorado, Jr. et al. |
| 10,308,886 B2 | 6/2019 | Rana et al. |
| 2001/0050700 A1 | 12/2001 | Smith et al. |
| 2002/0156136 A1 | 10/2002 | Hortrup et al. |
| 2003/0065177 A1 | 4/2003 | Sheridan et al. |
| 2003/0111331 A1 | 6/2003 | Chalfant et al. |
| 2003/0217418 A1 | 11/2003 | Fadel et al. |
| 2005/0209117 A1 | 9/2005 | Friedrich et al. |
| 2008/0045666 A1 | 2/2008 | Snell et al. |
| 2008/0090742 A1 | 4/2008 | Mathur |
| 2012/0056128 A1 | 3/2012 | Thoret Bauchet |
| 2013/0186629 A1 | 7/2013 | Leonard et al. |
| 2019/0117541 A1 | 4/2019 | Consoli et al. |
| 2020/0172831 A1 | 6/2020 | Dhawan et al. |
| 2020/0339503 A1 | 10/2020 | Dhawan et al. |
| 2020/0339880 A1 | 10/2020 | Masere et al. |

FOREIGN PATENT DOCUMENTS

| | | |
|---|---|---|
| EP | 0145588 A2 | 6/1985 |
| EP | 0449546 A1 | 10/1991 |
| GB | 748856 A | 5/1956 |
| GB | 2030581 A | 4/1980 |
| GB | 1567047 A | 5/1980 |
| JP | 6340570 A | 12/1994 |
| RU | 2046804 C1 | 10/1995 |
| WO | 2005037206 A2 | 4/2005 |
| WO | 2020113218 A2 | 6/2020 |

OTHER PUBLICATIONS

Habib et al. "Synthesis of Some Novel Antioxidantand Anticorrosive Additives for Egyptian Lubricating Oils" Petroleum Science and Technology, 30: pp. 2435-2449 (2012).

Ionova et al. "Synthesis, Structure, and Properties of New Antioxidants Based on Hydroxypropylated p-Aminodiphenylamine", Petroleum Chemistry, 51(6): pp. 454-457 (2011).

International Search Report issued in International Application No. PCT/US2021/056024, dated Feb. 16, 2022, 5 pages.

Written Opinion issued in International Application No. PCT/US2021/056024, dated Feb. 16, 2022, 9 pages.

International Search Report issued in International Application No. PCT/US2021/056028, dated Feb. 16, 2022, 5 pages.

Written Opinion issued in International Application No. PCT/US2021/056028, dated Feb. 16, 2022, 8 pages.

(HYDROXYALKYL)AMINOPHENOL POLYMERS AND METHODS OF USE

FIELD OF THE INVENTION

The present invention generally relates to polymeric compositions based on the condensation of phenolic compounds with aldehydes.

BACKGROUND

Polymeric compounds are used throughout industry to assist people in achieving important manufacturing and processing goals. Benefits in industrial processes such as inhibiting corrosion, inhibiting biofilm formation, inhibiting microbial growth, modifying rheology, emulsifying, demulsifying, tackifying, plasticizing, defoaming, flocculating, coagulating, and the like are achieved by practitioners using a variety of polymeric compounds. Thus, polymeric surfactants, emulsifiers, bio-film inhibitors, biocides, rheology modifiers, anti-corrodents, emulsion breakers, fuel dehazers, asphaltene dispersants, defoaming additives, flocculants/coagulants, and the like are generally available in the industry to append one or more industrial processes or assist in reaching one or more industrial manufacturing, processing, transporting, or storage goals.

An industrially important class of polymers is phenol-aldehyde type polymers, including prepolymers and cured resins (collectively "phenolic polymers" or "phenolics"). Phenolics are synthesized by condensing phenolic monomers such as phenol, resorcinol, Bisphenol A, alkylphenols, and/or mixtures of these with aldehydes such as formaldehyde. An industrially useful form of phenolic is a phenolic prepolymer. Phenolic prepolymers are commercially available as water-based dispersions including the partial reaction product of one or more phenolic monomers and formaldehyde. In such form, the prepolymer is relatively stable in the water dispersion. Since formaldehyde exists predominantly in solution as a dynamic equilibrium of methylene glycol oligomers, the concentration of the reactive form of any "free" formaldehyde residing in the prepolymer formulation depends on temperature and pH. Commercially available phenolic prepolymers include novalacs and resoles.

Novalacs are phenolic prepolymer dispersions wherein the molar ratio of formaldehyde to phenolic monomer is less than one, and wherein curing is accomplished using acid or base catalysis, in some embodiments employing heat, along with the addition of an aldehyde or a formaldehyde donor such as hexamethylene tetramine. Examples of suitable novalac cure catalysts include oxalic acid, hydrochloride acid, and sulfonic acid. The prepolymer units are mainly linked by methylene and/or ether groups through the methylolation of the phenolic monomer by the reactive form of formaldehyde. Resoles are phenolic prepolymer dispersions having a formaldehyde to phenolic monomer ratio of greater than one (for example, around 1.5). The resoles are cured after drying using heat and a base catalyst.

To form a phenolic prepolymer dispersion, phenolic monomer, aldehyde, water and catalyst are mixed in the desired amount and heated, for example to between about 50° C. and 100° C. or between about 60° C. and 80° C. to form the prepolymerized dispersion. The prepolymers will crosslink, in embodiments upon heating to around 120° C., to form methylene and dibenzyl ether bridges via elimination of both the water of dispersion and the water formed by the poly condensation reaction. The result is a stable, three-dimensional cured network. The final crosslinking step results in a phenolic resin possessing industrially recognized characteristics such as excellent hardness, thermal stability, and chemical imperviousness.

Alkylphenol-based phenolics, or "alkylphenolics" are structurally similar to phenolics formed from phenol and/or resorcinol and are synthesized using any of the foregoing processes wherein an alkylphenol is employed in place of, or in combination with, phenol, resorcinol, and the like. The alkylphenol monomer employed to synthesize the alkylphenolic is typically a 4-alkylphenol, e.g. 4-nonylphenol wherein the nonyl moiety is linear or branched. Alkylphenolic prepolymers and resins have improved solubility in hydrocarbon solvents compared to their non-alkylated counterparts. Industrially, alkylphenolics are employed to build green tack and impart adhesion strength in rubber-based adhesives, and are useful as modifiers for rubber materials such as butyl rubber, chloroprene rubber, and the like, imparting improved oil resistance, heat resistance, chemical resistance, and weathering properties to rubber products such as belts, treads, hoses, vehicle tires, and the like.

The alkylphenol monomer employed in the majority of industrial alkylphenolics is nonylphenol, which is often more accurately described as a highly branched C9 4-alkylphenol. Nonylphenol-formaldehyde condensation polymers provide a favorable solubility profile and cost effectiveness combination for industrial use. Cost effectiveness of the nonylphenol monomer is due to historically widespread industrial adoption of ethoxylated phenol surfactants, which are highly effective nonionic surfactants. However, nonylphenol and other alkylphenols, as the breakdown products of their ethoxylated adducts in the environment, have been restricted in many countries. Nonylphenols are now recognized to be endocrine disruptors and xenoestrogens in humans and aquatic animals. Accordingly, nonylphenol ethoxylates are being replaced by other surfactants, for example alkanol ethoxylates, in many international markets. Similarly, there is a need in the industry to replace alkylphenolics due to the desirability of eliminating use of alkylphenols generally and nonylphenols particularly.

Development of environmentally benign monomers that are usefully employed to form polymers possessing new and useful properties is an ongoing need in the industry. Further, there is a need to provide alternatives for alkylphenolics throughout the plethora of applications in which these compounds have found industrial utility.

SUMMARY OF THE INVENTION

Described herein are bis(hydroxycarbyl)aminophenolic ("HCAP") polymers, compositions including HCAP polymers, and methods of using the HCAP polymers. The HCAP polymers include an HCAP repeat unit according to Formula I:

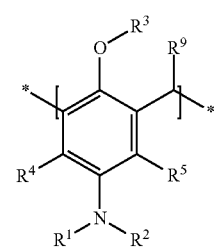

wherein $R^1$ and $R^2$ are —$(CR^6R^7)_n(CHOH)(CH_2)_p(O)_qR^8$; $R^3$ is H, alkyl, aryl, benzyl, or aralkyl; $R^4$ and $R^5$ are independently H, or $C_1$-$C_{22}$ alkyl, —OH, or —$NR_1R_2$; $R^6$ and $R^7$ are independently H or alkyl; $R^8$ is $C_1$-$C_{24}$ linear, branched, or cyclic alkyl, aryl, or aralkyl; $R^9$ is H, alkyl, aryl, benzyl, or aralkyl, optionally substituted with an alkyl group, alkoxy group, or hydroxyl group; n is an integer between 1 and 12; p is 0 or an integer between 1 and 12; and q is 0 or 1.

In embodiments, $R^3$ is H. In embodiments, $R^4$ and $R^5$ are H. In embodiments, $R^6$ and $R^7$ are H. In embodiments, $R^9$ is H. In embodiments, n, p, and q are 1. In embodiments, $R^8$ is n-octyl, isooctyl, n-decyl, isodecyl, n-hexyl, n-dodecyl, n-tetradecyl, n-hexadecyl, n-butyl, or 2-ethylhexyl. In embodiments, the HCAP polymer comprises 1-100 HCAP repeat units. In embodiments, the HCAP repeat unit is a first repeat unit, and the HCAP polymer is an HCAP copolymer further comprising a second repeat unit comprising the condensation product of a phenolic compound and an aldehyde. In embodiments, the phenolic compound is phenol, resorcinol, pyrocatechol, hydroquinone, phloroglucinol, hydroxyhydroquinone, or a mixture of two or more thereof.

In some embodiments, an HCAP polymer includes an HCAP repeat unit according to Formula II:

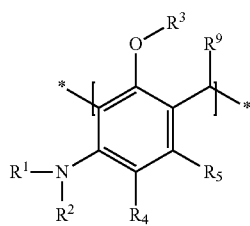

II wherein $R_1$, $R_2$, $R_3$, $R_5$, and $R_9$ are the same for Formulae I and II. In some embodiments, the HCAP polymer includes one or more HCAP repeat units according to Formula II and excludes HCAP repeat units according to Formula I. In other embodiments, the HCAP polymer includes one or more HCAP repeat units according to Formula I and excludes HCAP repeat units according to Formula II. In still other embodiments, the HCAP polymer includes one or more HCAP repeat units according to Formula I and one or more HCAP repeat units according to Formula II, and may be characterized as an HCAP copolymer. Thus, in embodiments, an HCAP copolymer comprises, consists essentially of, or consists of one or more HCAP repeat units of Formulae I, II, or a combination thereof. In embodiments, an HCAP copolymer comprises one or more HCAP repeat units of Formulae I, II, or a combination thereof; and one or more additional repeat units comprising the condensation product of a phenolic compound and an aldehyde. In some such embodiments, the one or more HCAP repeat units of Formulae I, II, or a combination thereof are first repeat units, and the HCAP copolymer further comprises a second repeat unit comprising the condensation product of a phenolic compound and an aldehyde. In embodiments, the phenolic compound is phenol, resorcinol, pyrocatechol, hydroquinone, phloroglucinol, hydroxyhydroquinone, or a mixture of two or more thereof. In embodiments, the aldehyde is formaldehyde, acetaldehyde, benzaldehyde, vanillin, salicylaldehyde, glyoxal, glyoxylic acid, or a mixture of two or more thereof.

In embodiments, the HCAP polymer is an HCAP prepolymer. In embodiments, the HCAP polymer is an HCAP resin. In embodiments, HCAP resins consist of, consist essentially of, or comprise stable, three-dimensional cured networks. HCAP resins possess industrially recognized characteristics such as excellent hardness, thermal stability, and chemical imperviousness. In embodiments, HCAP polymers exhibit antipolymerant or polymerization retardant properties when added to one or more sources of polymerizable species. Such sources include industrial process streams for producing e.g. styrene, isoprene, butadiene, or another ethylenically unsaturated monomer; and petroleum byproducts entrained or emulsified in water, including pygas, pytar, asphaltenes, and the like found in produced water and water quench systems in petroleum processing and reaction systems such as pyrolysis or ethylene cracking systems. In embodiments, HCAP resins exhibit bio-film inhibition properties. In embodiments, HCAP resins exhibit biocidal activity. In embodiments, HCAP resins are rheology modifiers for petroleum-based liquids and compounds dissolved or dispersed in petroleum-based liquids. In embodiments, HCAP resins are emulsion breakers for petroleum materials (such as asphaltenes or pygas products) entrained in water, or for inversion of water-in-oil polymer lattices in preparation for e.g. waterflooding (tertiary oil recovery) or other subterranean injection applications. In embodiments, the HCAP resins are dehazers for fuel compositions including diesel, gasoline, jet fuel and kerosene.

Other objects and features will be in part apparent and in part pointed out hereinafter.

DETAILED DESCRIPTION

Although the present disclosure provides references to preferred embodiments, persons skilled in the art will recognize that changes may be made in form and detail without departing from the spirit and scope of the invention. Various embodiments will be described in detail with reference to the drawings, wherein like reference numerals represent like parts and assemblies throughout the several views. Reference to various embodiments does not limit the scope of the claims attached hereto. Additionally, any examples set forth in this specification are not intended to be limiting and merely set forth some of the many possible embodiments for the appended claims.

Definitions

Unless otherwise defined, all technical and scientific terms used herein have the same meaning as commonly understood by one of ordinary skill in the art. In case of conflict, the present document, including definitions, will control. Preferred methods and materials are described below, although methods and materials similar or equivalent to those described herein can be used in practice or testing of the present invention. All publications, patent applications, patents and other references mentioned herein are incorporated by reference in their entirety. The materials, methods, and examples disclosed herein are illustrative only and not intended to be limiting.

As used herein, the term "foulant" means any one or more species that is present in an industrial process stream including hydrocarbon, water, or a mixture of these, and is capable of precipitation therefrom. Known foulants present in hydrocarbons such as crude oil include asphaltenes, waxes, heavy oil, tars, and aliphatic and aromatic hydrocarbons having a density less than that of water, and other dissolved or dispersed organic and inorganic solids. Other known foulants are byproducts of hydrocarbon reactive processes or a hydrocarbon refining processes, and include materials such as polynuclear aromatic hydrocarbons, coke, oxidized hydrocarbons, oligomers and polymers formed from polymerization of vinylic byproducts of hydrocarbon processing, such as styrene, butadiene, cyclopentadiene, and the like; and thermal decomposition products resulting from the degradation, aggregation, and/or polymerization of any of the foregoing or another foulant species present in an industrial process stream including hydrocarbon, water, or a mixture of these.

As used herein, the term "antifoulant" means any one or more compounds, or a composition including one or more compounds, that is effective to prevent precipitation of one or more foulants present within an industrial process stream. The antifoulant is present in the industrial process stream, or is added to the industrial process stream in an amount that is effective to prevent, reduce, or delay precipitation of one or more foulants from the industrial process stream. Accordingly, an antifoulant has "antifoulant properties" with respect to an industrial process stream in which it is effective to prevent, reduce, or delay precipitation of one or more foulants.

As used herein, the terms "comprise(s)," "include(s)," "having," "has," "can," "contain(s)," and variants thereof are intended to be open-ended transitional phrases, terms, or words that do not preclude the possibility of additional acts or structures. The singular forms "a," "and" and "the" include plural references unless the context clearly dictates otherwise. The present disclosure also contemplates other embodiments "comprising," "consisting of" and "consisting essentially of," the embodiments or elements presented herein, whether explicitly set forth or not.

As used herein, the term "optional" or "optionally" means that the subsequently described event or circumstance may but need not occur, and that the description includes instances where the event or circumstance occurs and instances in which it does not.

As used herein, the term "about" modifying, for example, the quantity of an ingredient in a composition, concentration, volume, process temperature, process time, yield, flow rate, pressure, and like values, and ranges thereof, employed in describing the embodiments of the disclosure, refers to variation in the numerical quantity that can occur, for example, through typical measuring and handling procedures used for making compounds, compositions, concentrates or use formulations; through inadvertent error in these procedures; through differences in the manufacture, source, or purity of starting materials or ingredients used to carry out the methods, and like proximate considerations. The term "about" also encompasses amounts that differ due to aging of a formulation with a particular initial concentration or mixture, and amounts that differ due to mixing or processing a formulation with a particular initial concentration or mixture. Where modified by the term "about" the claims appended hereto include equivalents to these quantities. Further, where "about" is employed to describe a range of values, for example "about 1 to 5" the recitation means "1 to 5" and "about 1 to about 5" and "1 to about 5" and "about 1 to 5" unless specifically limited by context.

As used herein, "substantially" means "consisting essentially of", as that term is construed in U.S. patent law, and includes "consisting of" as that term is construed in U.S. patent law. For example, a solution that is "substantially free" of a specified compound or material may be free of that compound or material, or may have a minor amount of that compound or material present, such as through unintended contamination, side reactions, or incomplete purification. A "minor amount" may be a trace, an unmeasurable amount, an amount that does not interfere with a value or property, or some other amount as provided in context. A composition that has "substantially only" a provided list of components may consist of only those components, or have a trace amount of some other component present, or have one or more additional components that do not materially affect the properties of the composition. Additionally, "substantially" modifying, for example, the type or quantity of an ingredient in a composition, a property, a measurable quantity, a method, a value, or a range, employed in describing the embodiments of the disclosure, refers to a variation that does not affect the overall recited composition, property, quantity, method, value, or range thereof in a manner that negates an intended composition, property, quantity, method, value, or range. Where modified by the term "substantially" the claims appended hereto include equivalents according to this definition.

As used herein, any recited ranges of values contemplate all values within the range and are to be construed as support for claims reciting any sub-ranges having endpoints which are real number values within the recited range. By way of a hypothetical illustrative example, a disclosure in this specification of a range of from 1 to 5 shall be considered to support claims to any of the following ranges: 1-5; 1-4; 1-3; 1-2; 2-5; 2-4; 2-3; 3-5; 3-4; and 4-5.

Discussion

Disclosed herein are bis(hydroxycarbyl)aminophenolic polymers ("HCAP polymers" or "HCAP resins"), which are polymeric compounds including one or more repeat units comprising the condensation product of a bis(hydroxycarbyl)aminophenolic compound (HCAP compound) with an aldehyde. In embodiments, HCAP compounds have one of the following structures:

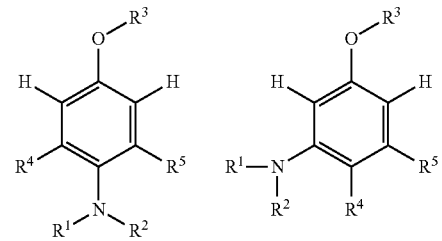

wherein $R^1$ and $R^2$ are $-(CR^6R^7)_n(CHOH)(CH_2)_p(O)_qR^8$, $R^3$ is H, alkyl, aryl, benzyl, or aralkyl; $R^4$ and $R^5$ are independently H, or $C_1$-$C_{22}$ alkyl, $-OH$, or $NR_1R_2$; $R^6$ and $R^7$ are independently H or alkyl; $R^8$ is $C_1$-$C_{24}$ linear, branched, or cyclic alkyl, aryl, or aralkyl; n is an integer between 1 and 12; p is 0 or an integer between 1 and 12; and q is 0 or 1. In embodiments, one or more of $R^4$ and $R^5$ is H or alkyl, wherein the HCAP compound is based on 4-aminophenol. In embodiments, one or more of $R^4$ and $R^5$ is H or $-OH$, further wherein the HCAP compound of Formula I is based on an aromatic hydroxylated compound such as 4-aminoresorcinol or phloroglucinol. In embodiments, $R^6$ and $R^7$ are H. In embodiments n, p, and q are each 1. In embodiments, $R^8$ is a $C_4$-$C_{18}$ linear or branched alkyl; in some such embodiments $R^8$ is n-octyl, isooctyl, n-decyl, isodecyl, n-dodecyl, n-tetradecyl, n-hexadecyl, n-hexyl, n-butyl, or 2-ethylhexyl.

In embodiments the HCAP compound is characterized as including an aromatic ring compound having a bis(hydroxycarbyl)amino adduct —N(R¹R²) bonded to the aromatic ring compound, at least one hydroxyl or alkoxyl group (phenolic hydroxyl group) bonded to the aromatic ring compound, and at least two hydrogen atoms susceptible to acid or base catalyzed condensation with an aldehyde bonded to the aromatic ring compound. Thus, in embodiments, the HCAP compound is a bis(hydroxycarbyl)amino adduct of, for example, phenol, resorcinol, pyrocatechol, hydroquinone, phloroglucinol, hydroxyhydroquinone, or another phenolic compound. All embodiments regarding the HCAP compounds, repeat units, polymers, and copolymers disclosed herein are intended to be freely combinable without limitation.

In some embodiments HCAP compounds are identified in copending U.S. application Ser. No. 16/860,954 as antipolymerants or polymerization retardants when added to industrial process streams for producing e.g. styrene, isoprene, butadiene, or another ethylenically unsaturated monomer. As such, the HCAP compounds are suitably employed to reduce free radical or oxidative type polymerization that occurs in such industrial process systems. However, we have found that the HCAP compounds are susceptible to condensation polymerization with an aldehyde to form a polymer having potential antipolymerant, polymerization retarding, or anti-fouling activity in systems for processing ethylenically unsaturated monomers; or for preventing fouling by polymerizable species within petroleum byproducts entrained or emulsified in water, including pygas, pytar, asphaltenes, and the like found in produced water and water quench systems in petroleum processing and reaction systems such as pyrolysis or ethylene cracking systems.

Accordingly, in embodiments, one or more HCAP compounds are condensed with an aldehyde such as formaldehyde (including paraformaldehyde and formalin), acetaldehyde, vanillin, ethylvanillin, glyoxal, glyoxylic acid, salicylaldehyde or benzaldehyde to provide a bis(hydroxycarbyl)aminophenolic polymer (HCAP polymer) comprising one or more HCAP repeat units. An HCAP repeat unit is characterized as including a bis(hydroxycarbyl)amino adduct —N(R¹R²), as defined for the HCAP compounds of Formula I. In embodiments, the HCAP repeat unit corresponds to Formula I,

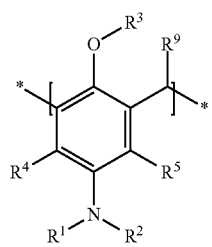

I wherein $R^1$, $R^2$, $R^3$, $R^4$, and $R^5$ are as defined above and $R^9$ is H, alkyl, aryl, benzyl, or aralkyl, optionally substituted such as with an alkyl group, alkoxy group, or hydroxyl group. All embodiments regarding the HCAP repeat units are intended to be freely combinable. In embodiments $R^9$ is H. In embodiments $R^9$ is CH$_3$. In embodiments $R^9$ is COOH. In embodiments $R^9$ is benzyl. In embodiments $R^9$ is

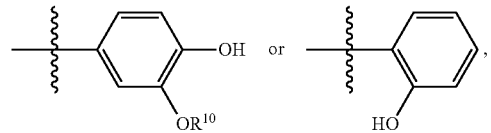

wherein $R^{10}$ is methyl or ethyl. In embodiments $R^9$ includes one or two oxygen atoms. In embodiments $R^9$ includes an ether moiety. In embodiments $R^9$ includes a hydroxyl moiety. In some embodiments $R^9$ includes one or more hydroxyl moieties, one or more ether moieties, or a combination thereof. In embodiments, $R^9$ includes a crosslink moiety, for example where glyoxal (a bisaldehyde) is employed as the aldehyde. Bisaldehydes include two aldehyde functionalities capable of condensation with HCAP functionalities and so are capable of obtaining crosslinking of the resulting HCAP polymer. In embodiments, one or more of $R^4$ and $R^5$ is H or —OH, further wherein the HCAP repeat unit is based on an aromatic hydroxylated compound such as resorcinol or phloroglucinol.

In embodiments of the repeat unit of Formula I, $R^3$ is H. In embodiments of the repeat unit of Formula I, $R^4$ is H. In embodiments of the repeat unit of Formula I, $R^5$ is H. In embodiments of the repeat unit of Formula I, $R^6$ is H. In embodiments of the repeat unit of Formula I, $R^7$ is H. In embodiments of the repeat unit of Formula I, two or more of $R^3$, $R^4$, $R^5$, $R^6$, and $R^7$ are H. In embodiments of the repeat unit of Formula I, $R^3$, $R^4$, $R^5$, $R^6$, and $R^7$, are H.

Further, in embodiments of the repeat unit of Formula I, $R^6$ and $R^7$ are H, n is 1, and q is 0. In some embodiments of the repeat unit of Formula I, $R^8$ is a branched alkyl group, an aryl group, or an aralkyl group. In some embodiments of the repeat unit of Formula I, $R^8$ is $C_4$-$C_{24}$ branched alkyl or $C_6$-$C_{24}$ aralkyl. In embodiments the repeat unit of Formula I includes n having a value of 0, 1, or 2. In embodiments the repeat unit of Formula II includes p having a value of 0, 1, or 2.

The HCAP repeat unit is characterized as including a bis(hydroxycarbyl)amino adduct defined by —N(R¹R²) as in Formula I. In some embodiments, the HCAP repeat unit is a repeat unit corresponding to a condensation product of an aldehyde with a bis(hydroxycarbyl)amino adduct of, for example, phenol, resorcinol, pyrocatechol, hydroquinone, phloroglucinol, hydroxyhydroquinone, or two or more thereof. All embodiments regarding the HCAP repeat units disclosed herein are intended to be freely combinable. In embodiments, an HCAP repeat unit is an HCAP repeat unit of Formula I. In embodiments, an HCAP polymer includes one or more HCAP repeat units in accordance with Formula I.

In embodiments, HCAP polymers are polymers including at least one HCAP repeat unit. In embodiments, HCAP polymers are formed by condensing one or more HCAP compounds with one or more aldehydes to form a polymer having at least 3 HCAP repeat units and up to 100 HCAP repeat units, for example a weight average or a number average of 3, 4, 5, 6, 7, 8, 9, 10, 15, 20, 25, 30, 35, 40, 45, 50, 55, 60, 65, 70, 75, 80, 85, 90, 95, or 100 HCAP repeat units or 3-10, 10-20, 20-30, 30-40, 40-50, 50-60, 60-70, 70-80, 80-90, or 90-100 HCAP repeat units or 3-90, 3-80, 3-70, 3-60, 3-50, 3-40, 3-30, 3-20, 3-15, 3-10, 3-9, 3-8, 3-7, 3-6, or 3-5 HCAP repeat units or 5-100, 10-100, 20-100, 30-100, 40-100, 50-100, 60-100, 70-100, 80-100, or 90-100 HCAP repeat units. In embodiments the HCAP polymer is formed by condensing an HCAP compound and formaldehyde and another aldehyde such as acetaldehyde or benzaldehyde, to form a HCAP polymer having at least 3 repeat units and up to 100 HCAP repeat units.

In embodiments, an HCAP polymer is an HCAP copolymer. In embodiments, HCAP copolymers include at least one HCAP repeat unit that is a first repeat unit, and a second repeat unit comprising a condensation product of a phenolic compound and an aldehyde selected from the aldehydes listed above, e.g. formaldehyde or an equivalent thereof (formalin or paraformaldehyde). Phenolic compounds are characterized as aromatic compounds having one or more hydroxyl groups bonded directly thereto. Phenolic compounds include, but are not limited to phenol, resorcinol, pyrocatechol, hydroquinone, phloroglucinol, and hydroxyhydroquinone. The HCAP copolymers include at least 3 total repeat units and up to 1000 repeat units, wherein at least one of the repeat units is an HCAP repeat unit. In some such embodiments the HCAP copolymers include 1-500 HCAP repeat units or 1-100 HCAP repeat units. In embodiments, the HCAP copolymer includes a repeat unit according to Formula I.

Combinations of the foregoing condensation strategies are advantageously employed to provide a wide compositional and structural range of HCAP polymer condensates. In embodiments the HCAP repeat unit includes two hydroxyalkyl moieties and one or more aromatic hydroxyl moieties per repeat unit. In embodiments an HCAP copolymer includes at least one HCAP repeat unit. In embodiments an HCAP homopolymer includes at least 3 HCAP repeat units. In embodiments, the weight average molecular weight of an HCAP polymer product is from about 200 Da to about 1,000,000 Da, such as 200 Da to 800,000 Da, 500 Da to 600,000 Da, 1,000 Da to 400,000 Da, 1,000 Da to 200,000 Da, 1,000 Da to 100,000 Da, 1,000 Da to 80,000 Da, 1,000 Da to 60,000 Da, 1,000 Da to 40,000 Da, 1,000 Da to 20,000 Da 5,000 Da to 800,000 Da, 5,000 Da to 600,000 Da, 5,000 Da to 400,000 Da, 5,000 Da to 200,000 Da, or 5,000 Da to 100,000 Da.

The number of HCAP repeat units in a homopolymer or copolymer condensate may be represented by m, wherein m is an integer or represents an average value, such as a weight average or number average value of 1 to 100 for a copolymer condensate or 3 to 100 for a homopolymer condensate. Thus, exemplary but non-limiting HCAP polymers include homopolymers and copolymers comprising one or more repeat units I(a)-I(e).

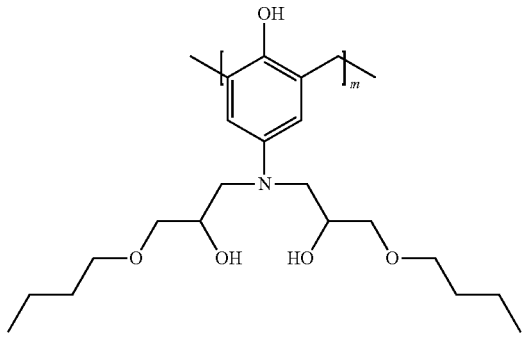

I(a)

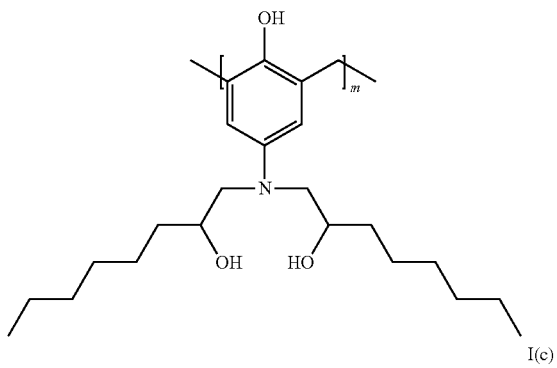

I(b)

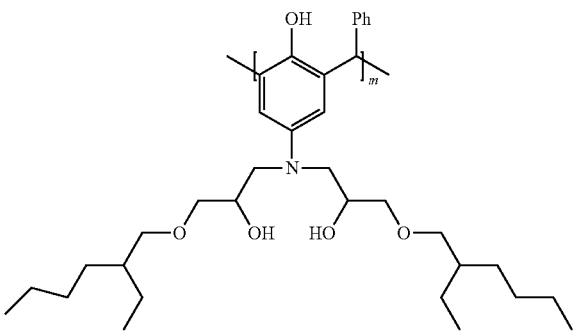

I(c)

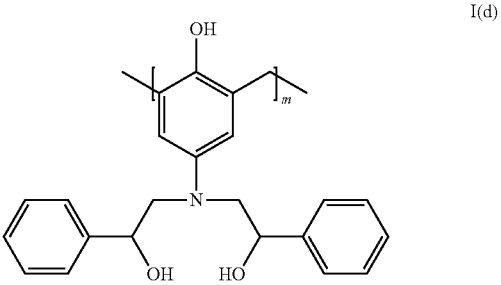

I(d)

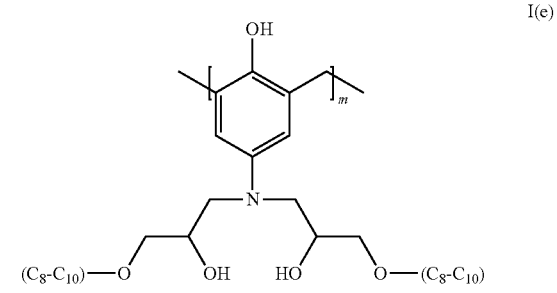

I(e)

The repeat unit I(a) is formed from the reaction of 4-aminophenol with butyl glycidyl ether, followed by condensation with formaldehyde. The repeat unit I(b) is formed by the reaction of 4-aminophenol with 1,2-epoxyoctane, followed by condensation with formaldehyde. The repeat unit I(c) is formed by the reaction of 4-aminophenol with 2-ethylhexylglycidyl ether, followed by condensation with benzaldehyde. The repeat unit I(d) is formed by the reaction of 4-aminophenol with styrene oxide, followed by condensation with formaldehyde. And the repeat unit I(e) is formed by the reaction of 4-aminophenol with a mixed $C_8$-$C_{10}$ alkyl glycidyl ether, followed by condensation with benzaldehyde; in some embodiments the mixed $C_8$-$C_{10}$ alkyl glycidyl ether includes a mixture of linear $C_8$-$C_{10}$ alkyl moieties, while in other embodiments the mixed $C_8$-$C_{10}$ alkyl glycidyl ether includes a mixture of linear and branched $C_8$-$C_{10}$ alkyl moieties.

In other exemplary but non-limiting embodiments, an HCAP polymer comprises one or more repeat units according to Formula II:

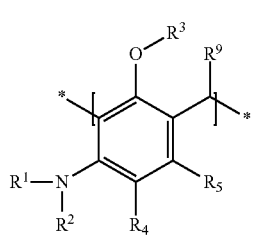

wherein $R_1$, $R_2$, $R_3$, $R_5$, and $R_9$ are the same for Formulae I and II. In embodiments, an HCAP polymer is an HCAP copolymer including one or more repeat units of both Formulae I and II. In some embodiments, the HCAP polymer includes one or more HCAP repeat units according to Formula II and excludes HCAP repeat units according to Formula I. In other embodiments, the HCAP polymer includes one or more HCAP repeat units according to Formula I and excludes HCAP repeat units according to Formula II. In still other embodiments, the HCAP polymer includes one or more HCAP repeat units according to Formula I and one or more HCAP repeat units according to Formula II, and may be characterized as an HCAP copolymer. Thus, in embodiments, an HCAP copolymer comprises, consists essentially of, or consists of one or more HCAP repeat units of Formulae I, II, or a combination thereof. In embodiments, an HCAP copolymer comprises one or more HCAP repeat units of Formulae I, II, or a combination thereof, and one or more additional repeat units comprising the condensation product of a phenolic compound and an aldehyde. In some such embodiments, the one or more HCAP repeat units of Formulae I, II, or a combination thereof are first repeat units, and the HCAP copolymer further comprises a second repeat unit comprising the condensation product of a phenolic compound and an aldehyde. In embodiments, the phenolic compound is phenol, resorcinol, pyrocatechol, hydroquinone, phloroglucinol, hydroxyhydroquinone, or a mixture of two or more thereof. In embodiments, the aldehyde is formaldehyde, acetaldehyde, benzaldehyde, vanillin, salicylaldehyde, glyoxal, glyoxylic acid, or a mixture of two or more thereof.

In embodiments, the synthesis of HCAP compounds is described in copending U.S. application Ser. No. 16/860,954. In embodiments, an HCAP is formed by a neat (solventless, 100% solids, or 100% actives) reaction of an aminophenolic compound, such as 4-aminophenol, with the selected epoxy-functional compound (typically but not always a glycidyl ether) in the selected molar ratio. In embodiments, about two moles of epoxy-functional compound are contacted with about one mole of the aminophenolic compound. In other embodiments, an excess molar amount of the epoxy-functional compound is employed in the reaction.

In embodiments, synthesis of HCAP compounds is accomplished by contacting the aminophenolic compound and the epoxy-functional compound at a temperature between 50° C. to 200° C. wherein contacting is accomplished using one or more of heating, stirring, adding one of the two reagents to the other using dropwise, batchwise, or continuous methods, excluding air, or substantially excluding air. In embodiments, substantially excluding air is achieved by blanketing or sparging the reaction vessel with an inert gas such as Ar or $N_2$. In some embodiments, the synthesis of HCAP is facilitated by further including a solvent, such as a petroleum-based solvent, in an amount of up to 100% volume based on the of the mass or volume of the combined reagents. In some embodiments, water is substantially excluded from the synthesis, in that no additional water is added to the reaction vessel.

In embodiments, once the HCAP compound is synthesized and optionally isolated by purification (such as by recrystallization and/or evaporation of solvent), it is condensed with an aldehyde to form an HCAP prepolymer, and the HCAP prepolymer is converted to an HCAP resin. In embodiments, one or more HCAP repeat units of the HCAP resin are HCAP repeat units according to formulae I or II or a combination thereof. The HCAP resin is an HCAP homopolymer or HCAP copolymer as described above.

Thus, an HCAP polymer or polymer product is defined herein as either an HCAP prepolymer or an HCAP resin. In embodiments, an HCAP prepolymer is formed by condensing aldehyde and phenolic content at mild temperature, such as below 100° C. to form an HCAP prepolymer; then the HCAP prepolymer is heated to remove the water of condensation and achieve cure (chain extension and/or crosslinking) to form an HCAP resin. In some embodiments, the ratio of aldehyde to total phenolic content is selected by the user to form a novalac type HCAP prepolymer, wherein the molar ratio of aldehyde to total phenolic content is less than 1. In some embodiments, the ratio of aldehyde to total phenolic content is selected by the user to form a resole type HCAP prepolymer, wherein the molar ratio of aldehyde to total phenolic content is greater than 1. In embodiments, the ratio of total phenolic content to aldehyde is selected by the user to be about 1:1. In some embodiments, the molar ratio of aldehyde to total phenolic content is between about 0.0005:1 to 0.8:1, or about 0.001 to 0.6:1, or about 0.1:1 to 0.4:1, or about 0.2:1 to 0.3:1. In other embodiments, the molar ratio of total phenolic content to aldehyde is between about 0.0005:1 to 0.8:1, or about 0.001 to 0.6:1, or about 0.1:1 to 0.4:1, or about 0.2:1 to 0.3:1.

In some embodiments the condensation reaction commonly employed in forming phenolic aldehyde prepolymers (novalacs and resoles) or cured phenolic resins are advantageously employed herein to form HCAP prepolymers and HCAP resins, including copolymeric prepolymers and/or resins. Specifically, one or more HCAP compounds or a combination of one or more HCAP compounds and one or more additional aromatic hydroxylated compounds are selected and combined with one or more aldehydes. Additional aromatic hydroxylated compounds include phenol, alkylated phenol, resorcinol, pyrocatechol, hydroquinone, phloroglucinol, hydroxyhydroquinone, lignosulfonic acid, phenoldisulfonic acid, and oligomerized sources such as tannic acid, humic acid, fulvic acid, lignin extracts, and Quebracho extracts; and other aromatic hydroxylated compounds without limitation. One or more HCAP compounds and optionally one or more additional aromatic compounds are combined to provide a "total phenolic content" or moles of reactive functionality available for condensation with an aldehyde.

Thus, in embodiments, a selected amount of total phenolic content is combined with a selected amount of one or more aldehydes, wherein the selections provide the desired level of polymerization; and a selected, acidic or basic cure catalyst is added under conditions of mild heat, for example between between 50° C. and 120° C., or between about 60° C. and 100° C. to obtain a polymeric condensation product or prepolymer. Suitable cure catalysts include sodium hydroxide, sulfuric acid, potassium hydroxide, triethylamine, oxalic acid, p-toluenesulfonic acid, p-dodecylbenzenesulfonic acid, methanesulfonic acid, dioctyl sulfosuccinate, or a cure catalyst resin such as resins sold by Georgia Pacific Corporation of Atlanta, Ga. under the trade name RESI-CAT®, such as GP® 012G23 RESI-CAT®. Acid or base catalysts are added to the reaction vessel in conventional amounts, for example 10 ppm to 7 wt % based on the weight of the reaction mixture, such as 10 ppm to 200 ppm, 200 ppm to 500 ppm, 500 ppm to 1000 ppm, 1000 ppm to 2000 ppm, 2000 ppm to 0.5 wt %, 0.5 wt % to 1 wt %, 1 wt to 2 wt %, 2 wt % to 5 wt %, 5 wt % to 7 wt %, 10 ppm to 1000 ppm, 10 ppm to 1 wt %, 100 ppm to 1 wt %, or 1000 ppm to 1 wt % based on the weight of the reaction mixture.

In embodiments, synthesis of the HCAP prepolymers is suitably carried out in an inert solvent. Since mild temperatures may be employed to initially react the aldehyde with the HCAP compound and any other aromatic hydroxylated compounds present, aromatic naphtha or paraffinic solvents or heavy aromatic naphtha may be employed as solvent. Petroleum based aromatic or paraffinic solvents, or fractionated or single-compound petroleum based solvents such as xylene are advantageously employed for mediation of the condensation reaction at 25% to 75% by volume based on combined mass of the aldehyde and the HCAP compound, such as 30% to 75%, or 40% to 75%, or 50% to 75%, or 60% to 75%, or 70% to 75%, or 25% to 70%, or 25% to 60%, or 25% to 50%, or 25% to 40% or 25% to 30% by volume based on combined mass of the aldehyde and the HCAP compound.

In embodiments, the synthesis of the HCAP prepolymers is carried out in the absence of added water. In embodiments, the synthesis of the HCAP prepolymers is carried out substantially in the absence of added water, wherein "substantially" means that sufficient water is added to the reaction vessel to achieve or enable a reaction such as depolymerization of paraformaldehyde or formalin to formaldehyde. In embodiments, synthesis of the HCAP prepolymers is achieved by addition of an acid or base catalyst to the reaction vessel along with an amount of water sufficient to dissolve and/or deliver the acid or base to the reaction vessel.

In embodiments, after the condensation is completed, an HCAP prepolymer is dispersed in a selected solvent. The selected solvent is preferably a hydrocarbon solvent or mixture thereof having a boiling point of greater than 100° C. The HCAP prepolymer is dispersed in the solvent at a total solids content of 30 wt % to 90 wt % based on the weight of the dispersion, or 35 wt % to 80 wt %, or about 40 wt % to 70 wgt %, or about 50 wt % to 60 wt % solids based on the weight of the dispersion. The HCAP prepolymers are suitably converted to HCAP resins by heating the prepolymer dispersion to at least 100° C., such as 100° C. to 180° C., or 120° C. to 150° C. The higher temperature in this stage causes methylene and dibenzyl ether bridges to form via elimination of the water formed by the condensation reaction. The HCAP prepolymers chain-extend, crosslink, or both (collectively, "cure"), in some embodiments concomitant with evaporation of the solvent, such as by coating and evaporative heating, to result in an HCAP resin. In other embodiments, the HCAP prepolymer is cured by heating in the solvent, wherein the water of condensation is removed from the reaction vessel by azeotrope or by use of molecular sieves or another drying agent.

The HCAP resins are stable, three-dimensional cured networks. The HCAP resins possess industrially recognized characteristics such as excellent hardness, thermal stability, and chemical imperviousness. In embodiments, the HCAP resins exhibit antifouling properties when added to one or more sources of polymerizable species. Such sources include, in various embodiments, industrial process streams for producing e.g. styrene, isoprene, butadiene, or another ethylenically unsaturated monomer; and petroleum byproducts entrained or emulsified in water, including pygas, pytar, asphaltenes, and the like found in produced water and water quench systems in petroleum processing and reaction systems such as pyrolysis or ethylene cracking systems. In embodiments, HCAP resins exhibit bio-film inhibition properties, or biocidal activity. In embodiments, HCAP resins are rheology modifiers for petroleum-based liquids and compounds dissolved or dispersed in petroleum based liquids. In embodiments, the HCAP resins are useful as emulsion breakers for petroleum materials (such as asphaltenes or pygas products) entrained in water, or for inversion of water-in-oil polymer lattices in preparation for e.g. waterflooding (tertiary oil recovery) or other subterranean injection applications. In embodiments, the HCAP resins are useful as dehazers for fuel compositions including diesel, gasoline, jet fuel and kerosene.

The HCAP resins described herein include one or more HCAP repeat units. The HCAP repeat units include at least two alkanolic hydroxyl groups, incorporated into the backbone of the HCAP polymer as (hydroxycarbyl)amino moieties. In embodiments the HCAP repeat units, or another repeat unit of an HCAP polymer, or a combination thereof further include one or more aromatic (phenolic) hydroxyl moieties. HCAP hydroxyl moieties incorporated within the HCAP polymer backbone are available for functionalization thereof to impart one or more additional properties to the HCAP resin or to change one or more properties of the HCAP resin. Thus, in embodiments, one or more HCAP resins are suitably functionalized by reaction of the alkanolic and/or aromatic hydroxyl groups to bond one or more adducts bonded thereto, to form a functionalized HCAP resin.

In embodiments, one or more HCAP resins are suitably combined with one or more additional components to provide an HCAP composition. Thus, in embodiments, an HCAP composition comprises, consists essentially of, or consists of one or more HCAP resins and one or more additional components. In embodiments, the one or more additional components comprise, consist essentially of, or consist of a solvent. In embodiments, the solvent is selected from toluene, heavy aromatic naphtha, xylenes, a glycol, water, an alcohol, ethylene glycol, ethylene glycol monobutyl ether, kerosene, propylene carbonate, a glycol ether, or any combination thereof. In some embodiments, the alcohol is selected from methanol, ethanol, isopropanol, 2-ethyl hexanol, benzyl alcohol, or any combination thereof. In some embodiments, the glycol is ethylene glycol or a glycol ether, such as ethylene glycol monobutyl ether, or any combination thereof. In some embodiments, the HCAP composition excludes an alkylphenol and/or an alkylphenol alkoxylate.

In some embodiments, one or more additional components present in or added to the HCAP compositions disclosed herein include one or more corrosion inhibitors, viscosity reducers, friction reducers, scale inhibitors, clay swelling inhibitors, biocides, dispersants, flow back aids, emulsifiers, emulsion breakers, hydrogen sulfide scavengers, hydrate inhibitors, pH modifiers, surfactants, and/or other chemical treatment additives known to one of skill in the art of crude oil production, refining and chemical processing.

In embodiments, an HCAP composition includes at least 5 wt % and up to 99.9 wt % of the one or more HCAP polymers and 0.01 wt % to 95 wt % of the one or more additional components, based on total weight of the composition, such as 0.01 wt % to 90 wt %, 0.01 wt % to 80 wt %, 0.01 wt % to 70 wt %, 0.01 wt % to 60 wt %, 0.01 wt % to 50 wt %, 0.01 wt % to 40 wt %, 0.01 wt % to 30 wt %, 0.01 wt % to 20 wt %, 0.01 wt % to 10 wt %, 0.01 wt % to 5 wt %, 0.01 wt % to 4 wt %, 0.01 wt % to 3 wt %, 0.01 wt % to 2 wt %, 0.01 wt % to 1 wt %, or 0.01 wt % to 0.1 wt % of a total of the one or more additional components based on total weight of the composition. The one or more additional components are suitably admixed with one or more HCAP resins in any order to obtain the HCAP compositions.

In accord with the foregoing disclosures, one or more HCAP resins, or a composition including one or more HCAP resins, are usefully added to one or more industrial process streams to provide one or more benefits to the industrial process stream when compared to the same industrial process stream in the absence of the one or more HCAP resins. Such benefits include obtaining one or more of the following properties or effects: antifouling, antipolymerization, rheology modification, bio-film inhibition, biocidal activity, dehazing, emulsion breaking, and increased yield in tertiary oil recovery.

Thus, in embodiments, one or more HCAP resins or a composition including one or more HCAP resins are suitably added to an industrial process stream including one or more foulants, and the HCAP resin has antifouling properties when added thereto. In embodiments, foulants comprise or consist essentially of asphaltenes, waxes, or a combination of these; and the one or more HCAP resins, or a composition including one or more HCAP resins with one or more additional components is effective as an antifoulant when added to the industrial process stream. In embodiments, one or more HCAP resins, or a composition including one or more HCAP resins with one or more additional components is suitably added to an industrial process stream comprising or consisting essentially of one or more polymerizable species. In embodiments, polymerizable species include one or more of styrene, isoprene, butadiene, or another ethylenically unsaturated monomer, wherein the HCAP resin or a composition including an HCAP resin with one or more additional components obtains antifoulant properties when added thereto. The antifoulant properties of the one or more HCAP resins prevent precipitation of one or more foulants onto one or more surfaces present within an industrial processing system used for manufacture or processing operations carried out on the industrial process stream, such as the surfaces of metal pipes, pumps, heating or cooling apparatuses, and other portions and surfaces of the industrial processing system contacted by the industrial process stream during the manufacturing or processing.

In embodiments, an industrial process stream including one or more foulants comprises, consists essentially of, or consists of one or more hydrocarbon compounds. In some such embodiments, the one or more hydrocarbon compounds are a crude oil, or are present in a crude oil. In embodiments, the industrial process stream including one or more foulants is crude oil. In other embodiments, the industrial process stream including one or more foulants is a reaction product or a refined petroleum product resulting from one or more industrial processes carried out on the industrial process stream prior to concomitant with the addition of one or more HCAP resins, or a composition including one or more HCAP resins to the industrial process stream.

In some embodiments where the industrial process stream including one or more foulants comprises, consists essentially of, or consists of one or more hydrocarbon compounds, the foulant is a wax. Petroleum waxes are generally solid or semisolid, crystalline or semicrystalline $C_{20}$-$C_{50}$ hydrocarbons that occur naturally in crude oil and reside in some refined or reacted products thereof. The antifoulant properties of the one or more HCAP resins prevent precipitation of one or more waxes present in the industrial processing stream onto one or more surfaces present within an industrial hydrocarbon processing system, such as surfaces of metal pipes, pumps, heating apparatuses, and other portions and surfaces contacted by one or more waxes present within the industrial processing stream. The antifoulant properties of the one or more HCAP resins prevent precipitation of one or more waxes present in the industrial processing stream during batchwise storage and transportation of the industrial processing stream, such as storage and transportation of the industrial processing stream in metal or plastic containments. The storage or transportation containment is any container or vessel used to store or transport a crude oil or a hydrocarbon or mixture thereof, including, but not limited to, a storage tank, rail car, tank truck, marine vessel, barge, or pipeline.

In embodiments, an industrial process stream including one or more foulants comprises, consists essentially of, or consists of a produced water. In embodiments, the industrial process stream including one or more foulants comprises, consists essentially of, or consists of a quench water. Quench waters and produced waters are industrial process streams comprising one or more petroleum byproducts entrained, dispersed, or emulsified in water, wherein the one or more byproducts include pygas, pytar, asphaltenes, or mixtures of these. Quench water is located within water quench systems for petroleum processing and reaction systems such as pyrolysis or ethylene cracking systems, wherein one or more HCAP resins or a composition including one or more HCAP resins is effective as an antifoulant when added to the quench water, compared to the same quench water in the absence of the one or more HCAP resins. The antifoulant properties of the one or more HCAP resins prevent precipitation of one or more foulants onto one or more surfaces present within the water quench system, such as surfaces of metal pipes, pumps, heating apparatuses, and other portions and surfaces of the water quench system contacted by one or more foulants therein. Produced water, also called "connate", is native water obtained during petroleum recovery processes along with crude oil, and includes one or more petroleum byproducts entrained therein, and often also includes 0.1 wt % and as much as 30 wt % total dissolved solids dispersed therein, which in some embodiments further includes materials such as organic and inorganic debris and salts including calcium salts.

In embodiments, HCAP resins are rheology modifiers for industrial process streams comprising, consisting essentially of, or consisting of petroleum-based liquids and compounds dissolved or dispersed in petroleum-based liquids. Thus, when one or more HCAP resins, or a composition including one or more HCAP resins with one or more additional components is added in an effective amount to such an industrial process stream, the HCAP resins reduce or eliminate increases in the viscosity of the petroleum-based liquid during storage thereof—that is, over time—when compared to the same industrial process stream in the absence of the one or more HCAP resins. In embodiments, HCAP resins are dehazers for industrial process streams comprising, consisting essentially of, or consisting of fuel compositions, including diesel, gasoline, jet fuel and kerosene. Thus, when one or more HCAP resins, or a composition including one or more HCAP resins with one or more additional components are added in an effective amount to such an industrial process stream, the one or more HCAP resins reduce or eliminate observed loss of clarity and development of haze in the fuel compositions that develop during storage thereof—that is, over time—when compared to the same industrial process stream in the absence of the one or more HCAP resins.

In embodiments, one or more HCAP resins or a composition including one or more HCAP resins is added continuously to an industrial process stream such as any of the foregoing industrial process streams. In embodiments, one or more HCAP resins or a composition including one or more HCAP resins is added intermittently or semi-continuously to an industrial process stream such as any of the foregoing industrial process streams. In embodiments, one or more HCAP resins or a composition including one or more HCAP resins is added batchwise to an industrial process batch, which is a discrete volume of one or more of any of the foregoing industrial process streams. In some embodiments, the amount of the composition applied to a selected industrial process stream over a selected unit of time is fixed. In other embodiments, the amount of the composition applied to a selected industrial process stream over a selected unit of time is variable.

In embodiments, one or more HCAP resins are suitably added to an industrial process stream, such as any of the foregoing industrial process streams, in an amount of 0.1 ppm to 10,000 ppm based on a volume of the industrial process stream. In embodiments, one or more HCAP resins are suitably added to an industrial process stream, such as any of the foregoing industrial process streams, in an amount of 0.1 ppm to 10,000 ppm based on a weight of the industrial process stream. In embodiments, an HCAP composition comprising one or more HCAP resins is suitably added to an industrial process stream, such as any of the foregoing industrial process streams, in an amount corresponding to 0.1 ppm to 10,000 ppm of the one or more HCAP resins, based on a volume or based on a weight of the industrial process stream. In any of these embodiments, one or more HCAP resins are suitably added to or an industrial process stream, such as any of the foregoing industrial process streams, in an amount of 0.1 ppm to 10,000 ppm, 0.1 ppm to 8,000 ppm, 0.1 ppm to 6,000 ppm, 0.1 ppm to 4,000 ppm, 0.1 ppm to 2,000 ppm, 0.1 ppm to 1,000 ppm, 0.1 ppm to 500 ppm, 0.1 ppm to 250 ppm, 0.1 ppm to 100 ppm, 0.1 ppm to 50 ppm, 0.1 ppm to 40 ppm, 0.1 ppm to 30 ppm, 0.1 ppm to 20 ppm, 0.1 ppm to 10 ppm, 0.1 ppm to 5 ppm, 0.1 ppm to 1 ppm, 1 ppm to 10,000 ppm, 1 ppm to 8,000 ppm, 1 ppm to 6,000 ppm, 1 ppm to 4,000 ppm, 1 ppm to 2,000 ppm, 1 ppm to 1,000 ppm, 1 ppm to 500 ppm, 1 ppm to 250 ppm, 1 ppm to 100 ppm, 1 ppm to 50 ppm, 1 ppm to 40 ppm, 1 ppm to 30 ppm, 1 ppm to 20 ppm, 1 ppm to 10 ppm, or 1 ppm to 5 ppm, based on volume of the industrial process stream or based on the weight of the industrial process stream.

In accord with the foregoing, one or more HCAP resins are included in a treated industrial process stream composition. A treated industrial process stream comprises one or more HCAP resins, and an industrial process stream comprising a foulant. In embodiments the industrial process stream comprises, consists essentially of, or consists of hydrocarbons. In embodiments, the treated industrial process stream comprises about 0.1 ppm to about 10,000 ppm of the one or more HCAP resins based on either the volume or the weight of the treated process stream, such as 0.1 ppm to 10,000 ppm, 0.1 ppm to 8,000 ppm, 0.1 ppm to 6,000 ppm, 0.1 ppm to 4,000 ppm, 0.1 ppm to 2,000 ppm, 0.1 ppm to 1,000 ppm, 0.1 ppm to 500 ppm, 0.1 ppm to 250 ppm, 0.1 ppm to 100 ppm, 0.1 ppm to 50 ppm, 0.1 ppm to 40 ppm, 0.1 ppm to 30 ppm, 0.1 ppm to 20 ppm, 0.1 ppm to 10 ppm, 0.1 ppm to 5 ppm, 0.1 ppm to 1 ppm, 1 ppm to 10,000 ppm, 1 ppm to 8,000 ppm, 1 ppm to 6,000 ppm, 1 ppm to 4,000 ppm, 1 ppm to 2,000 ppm, 1 ppm to 1,000 ppm, 1 ppm to 500 ppm, 1 ppm to 250 ppm, 1 ppm to 100 ppm, 1 ppm to 50 ppm, 1 ppm to 40 ppm, 1 ppm to 30 ppm, 1 ppm to 20 ppm, 1 ppm to 10 ppm, or 1 ppm to 5 ppm of the one or more HCAP resins based on either the volume or the weight of the treated process stream. In some embodiments, the treated industrial process stream is disposed within an industrial processing system.

In embodiments, a treated industrial process stream is stable at a temperature of about 20° C. to about 400° C., meaning that the HCAP resins do not substantially degrade or undergo substantial thermochemical conversion within the stated temperature range when subjected to industrial processes requiring these temperatures. In some embodiments, treated industrial process stream is disposed within an industrial processing system, and the treated industrial process stream is then subjected to temperatures between 20° C. and 400° C. That is, the treated industrial process stream is in contact with an industrial processing system during the subjecting, and the antifoulant properties of the HCAP resins are not reduced, or are not substantially reduced. By "not substantially reduced" it is meant that the antifoulant properties of the HCAP resins subjected to temperatures of up to 400° C. are reduced by less than 10% by the subjecting, based on the initial antifoulant properties and using any measurement methods known to those of skill in the art of measuring fouling of industrial processing systems.

In embodiments, the HCAP resins or HCAP compositions or both are thermolytically stable under conditions commonly employed or encountered within hydrocarbon process streams. Thus, in embodiments, one or more HCAP resins or HCAP compositions are added to one or more hydrocarbon processing streams prior to subjecting the treated hydrocarbon processing stream to one or more thermolytically challenging processes, such as hydrotreating. The HCAP resins retain their antifouling properties during hydrocarbon processing at temperatures of about 20° C. to 400° C. Further, the HCAP resins are hydrolytically stable and not susceptible to hydrolysis even at temperatures above 100° C. and therefore are suitable for use in hydrocarbon processing streams comprising water, including liquid water or steam.

In embodiments, a treated industrial process stream in accord with the any of the foregoing uses or applications undergoes at least a 20% reduction in fouling (precipitation of foulants or waxes) and as much as a 100% reduction in fouling when compared to the corresponding industrial process stream (that is, the untreated process stream), such as a 30% to 100% reduction in fouling, or 40% to 100%, 50% to 100%, 60% to 100%, 70% to 100%, 80% to 100%, 90% to 100%, 95% to 100% reduction in measurable fouling of industrial processing system surfaces contacted by the treated industrial process stream, as compared to industrial processing system surfaces contacted by the corresponding untreated industrial process stream.

In embodiments, a reduction in fouling may be determined by the following test. A selected volume of a treated industrial process stream is added to hexane or heptane, and the diluted treated industrial process stream is allowed to stand for 2 hours at about 20° C. Any precipitate that forms in the diluted treated industrial process stream is measured volumetrically and reported as a percentage of the precipitate observed in the control sample, which is the corresponding untreated industrial process stream, similarly diluted with hexane or heptane. Fouling may be measured as a relative increase in amount of precipitated solids by weight or volume obtained from the diluted treated industrial process stream at the end of the 2 hour period, when compared to the retention of solids in the untreated industrial process stream over the same period of time. Fouling may also be measured as a relative decrease in the weight or volume of precipitate arising from a selected period of contact of a treated industrial process stream within or disposed in an industrial process system, relative to the same period of contact of the industrial process system with the corresponding untreated industrial process stream.

In some embodiments, the treated industrial process stream is added to, or is disposed within an industrial process system, the system comprising an interior surface, wherein the treated hydrocarbon stream is in fluid contact with the interior surface. In embodiments the interior surface comprises, consists essentially of, or consists of metal. In embodiments the industrial process system includes items for removing hydrocarbon products from a subterranean reservoir, for transporting one or more hydrocarbon products from a first location to a second location, or for separating, refining, treating, isolating, distilling, reacting, metering, heating, cooling, or containing one or more hydrocarbon products.

EXPERIMENTAL

Example 1

A 500 mL three necked round-bottom flask was equipped with temperature probe, nitrogen inlet, condenser and magnetic stir bar. Then 190 g 2-ethylhexylglycidyl ether was added to the flask. Then 4-aminophenol was added to flask with good stirring. The mixture was heated to 120° C. under nitrogen blanket and stirred for about 1 hour or until completion of reaction. As reaction proceeded a homogenous dark-amber product was observed to form. The resulting product was characterized by NMR and ESI-MS to have the following structure:

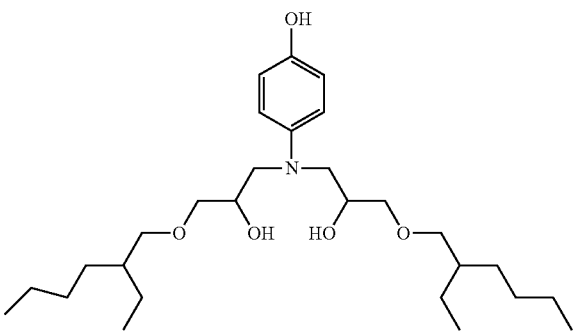 [SMILES: CCCCC(CC)COCC(O)CN(CC(O)COCC(CC)CCCC)c1ccc(O)cc1]

Example 2

The procedure of Example 1 was repeated using butyl glycidyl ether in a 1:1 molar replacement of 2-ethylhexylglycidyl ether. The polymeric product was analyzed by gel permeation chromatography and was found to have a weight average molecular weight of 6996 g/mol and a polydispersity index of 4.9.

Example 3

The procedure of Example 1 was repeated using $C_8$-$C_{10}$ (average carbon chain length) alkyl glycidyl ether in a 1:1 molar replacement of 2-ethylhexylglycidyl ether. The polymeric product was analyzed by gel permeation chromatography and was found to have a weight average molecular weight of 6157 g/mol and a polydispersity index of 3.0.

Example 4

A 1 L four-necked round bottom flask was equipped with an overhead stirrer, $N_2$ purge, temperature probe, and Dean-Stark trap with condenser. Example 1 was repeated, and the entire product obtained was added to the flask, along with 290 g heavy aromatic naphtha (HAN) and 1.5 g of a 50% KOH solution. The overhead stirrer was started along with a very slow nitrogen purge (approximately one bubble per five seconds). The reaction flask was heated to 65° C. Then 20 g of paraformaldehyde was prepared for addition to the flask. Once a consistent temperature of 65° C. was achieved, a first aliquot (about 10 g) of the paraformaldehyde was added to the flask. The temperature was observed to increase 15° C.-20° C. When the exotherm stopped and the reactor returned to 65° C., the remainder of the 20 g of paraformaldehyde was added to the flask. The temperature was observed to increase 1° C.-10° C.

When the exotherm stopped, the set temperature in the flask was changed from 65° C. to 95° C. The flask was then held at 95° C. for 3 hours.

After the 3 hours elapsed, the set temperature of the flask was increased to 180° C. whereupon reflux was observed. Reflux was continued for three hours. At the end of the three-hour reaction period, the heat source was removed and the flask was allowed to cool overnight. The amount of water removed via the Dean-Stark trap was recorded.

The polymeric product was analyzed by gel permeation chromatography and was found to have a weight average molecular weight of 4574 g/mol and a polydispersity index of 2.2.

Example 5

A 1 L four-necked round bottom flask was charged with p-N,N-di-[1-(2-ethylhexyloxy)-2-hydroxy-propyl)] aminophenol/formaldehyde resin made by the procedure of Example 1 and potassium hydroxide; the flask was equipped with an overhead stirrer, a nitrogen purge, a Dean-Stark trap with condenser, and a temperature probe. The stirrer was started at moderate speed, as the nitrogen purge was started at a rate of one bubble per second. The water flow was turned on to the condenser and the Dean-Stark trap was filled to the neck with heavy aromatic naphtha. The temperature was set to 150° C. and heating was started. Water was distilled from the base catalyst. A 5 mL sample was collected for Karl-Fischer water analysis. If the sample contained more than 0.1% water, distillation was continued for 30 minutes and analysis was repeated. When the sample contained less than 0.1% water, the flask was cooled to 60° C. Once the reaction mixture reached 60° C., the N₂ purge was increased.

Example 6

The procedure of Example 1 was repeated using 2-ethylhexylglycidyl ether or another alkyl glycidyl ether in a 1:1 molar replacement thereof, to make polymer resins AD-1 to AD-6 as shown in Table 1. The resins were analyzed by gel permeation chromatography, and weight average molecular weight and a polydispersity index of the resins are reported in Table 1.

TABLE 1

Weight average molecular weight and polydispersity index of resins AD-1 to AD-6 of Example 7.

| Resin | Alkyl group of alkyl glycidyl ether | Mw (Daltons) | PDI |
|---|---|---|---|
| AD-1 | Butyl | 6996 | 4.9 |
| AD-2 | 2-ethylhexyl | 6998 | 3.3 |
| AD-3 | linear C8-C10 alkyl | 20731 | 6.4 |
| AD-4 | linear C8-C10 alkyl | 6157 | 3.0 |
| AD-5 | 2-ethylhexyl | 4574 | 2.2 |
| AD-6 | 2-ethylhexyl | 3353 | 2.1 |

Resins AD-1 to AD-6 were then tested for effectiveness as asphaltene dispersants. The desired result of such testing is low to no precipitation of asphaltene materials when the resins are mixed with a crude (unrefined) oil product having asphaltene materials dispersed therein. Precipitation of solids from crude oil mixtures is predictive of relative fouling behavior in petroleum process streams. Accordingly, since the testing employs actual crude oil material, a blank (no dispersant) as well as conventional industry asphaltene dispersants were tested side-by-side to show the comparative effectiveness of the resins AD-1 to AD-6 to prevent precipitation.

Accordingly, to test each of the resins, a 15 mL graduated, conical centrifuge tube was charged with 100 µL of a crude oil having 20.3° API Gravity, to which 10 ppm of the resin by weight (actives) was added, then 10 mL n-heptane was added to the tube. Then the tube was thoroughly mixed by hand until all of the oil appeared to be dispersed. Then the tube was placed in a test tube rack at ambient laboratory temperature and allowed to stand for two hours, and at the end of the two hours the volume of sediment in the tube was recorded. Observed volume of sediment in each of the centrifuge tubes at the end of the two hours is reported in Table 2.

In addition to testing each of the resins AD-1 to AD-6 using the foregoing procedure, a blank (no dispersant) was made for comparison; and two conventional industry asphaltene dispersants were also tested for comparative purposes by adding 10 ppm by weight of actives as reported by the manufacturer of EC3019C and EC3238A, formulations obtained from Ecolab Inc. of St. Paul, Minn. Observed volume of sediment in each of the centrifuge tubes at the end of the two hours is reported in Table 2.

TABLE 2

Observed volume of sediment formed in 10 mL test formulations including AD-1 to AD-6.

| Resin | Test Description | Mw (Daltons) | PDI | Sediment (mL) |
|---|---|---|---|---|
| None (Blank) | No dispersant | | | 0.6 |
| EC3019C | Commercial asphaltene dispersant | | | 0.1 |
| EC3238A | Commercial asphaltene dispersant | | | 0.5 |
| AD-1 | Alkyl = butyl | 6996 | 4.9 | 0.4 |
| AD-2 | Alkyl = 2-ethylhexyl | 6998 | 3.3 | 0.05 |
| AD-3 | Alkyl = C8-C10 | 20731 | 6.4 | 0.1 |
| AD-4 | Alkyl = C8-C10 | 6157 | 3.0 | 0.05 |
| AD-5 | Alkyl = 2-ethyhexyl | 4574 | 2.2 | 0.15 |
| AD-6 | Alkyl = 2-ethylhexyl | 3353 | 2.1 | 0 |

Compared to the commercial asphaltene dispersants, resins AD-2, AD-3, AD-4, AD-5, and AD-6 were found to be as effective or more effective in preventing precipitation; and AD-1 was as effective or more effective than commercial asphaltene dispersant EC3238A.

What is claimed is:

1. A polymer comprising a repeat unit having the structure of Formula I, Formula II, or a combination thereof,

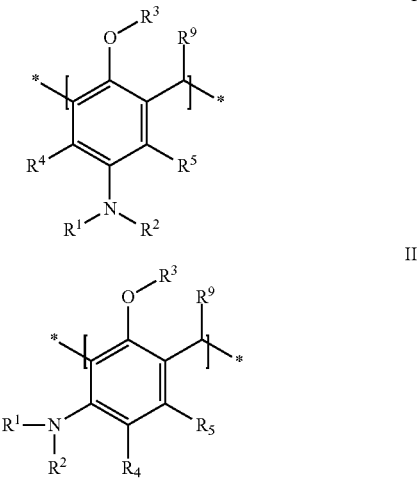

wherein $R^1$ and $R^2$ are $-(CR^6R^7)_n(CHOH)(CH_2)_p(O)_qR^8$; $R^3$ is H, alkyl, aryl, benzyl, or aralkyl; $R^4$ and $R^5$ are independently H, or $C_1$-$C_{22}$ alkyl, $-OH$, or $NR_1R_2$; $R^6$ and $R^7$ are independently H or alkyl; $R^8$ is $C_1$-$C_{24}$ linear, branched, or cyclic alkyl, aryl, or aralkyl; $R^9$ is H, alkyl, aryl, benzyl, or aralkyl, optionally substituted with an alkyl group, alkoxy group, or hydroxyl group; n is an integer between 1 and 12; p is 0 or an integer between 1 and 12; and q is 0 or 1.

2. The polymer of claim 1 wherein $R^3$ is H.
3. The polymer of claim 1 wherein $R^4$ and $R^5$ are H.
4. The polymer of claim 1 wherein $R^6$ and $R^7$ are H.
5. The polymer of claim 1 wherein $R^9$ is H.
6. The polymer of claim 1 wherein n, p, and q are 1.
7. The polymer of claim 1 wherein $R^8$ is n-octyl, isooctyl, n-decyl, isodecyl, n-hexyl, n-butyl, or 2-ethylhexyl.
8. The polymer of claim 1 comprising 1-100 of the repeat units.

9. The polymer of claim 1 further comprising an additional repeat unit comprising the condensation product of a phenolic compound and an aldehyde.

10. The polymer of claim 9 wherein the phenolic compound is phenol, resorcinol, pyrocatechol, hydroquinone, phloroglucinol, hydroxyhydroquinone, or a mixture of two or more thereof.

11. The polymer of claim 9 wherein the aldehyde is formaldehyde, acetaldehyde, benzaldehyde, vanillin, salicylaldehyde, glyoxal, glyoxylic acid, or a mixture of two or more thereof.

12. The polymer of claim 1 wherein the polymer excludes repeat units having the structure of Formula II.

13. A composition comprising the polymer of claim 1 and a solvent selected from toluene, heavy aromatic naphtha, xylenes, a glycol, water, an alcohol, ethylene glycol, ethylene glycol monobutyl ether, kerosene, propylene carbonate, a glycol ether, or any combination thereof.

14. The composition of claim 13 further comprising one or more corrosion inhibitors, viscosity reducers, friction reducers, scale inhibitors, clay swelling inhibitors, biocides, dispersants, flow back aids, emulsifiers, emulsion breakers, hydrogen sulfide scavengers, hydrate inhibitors, pH modifiers, or surfactants.

15. The composition of claim 13 wherein the composition comprises 5 wt % to 99.9 wt % of the polymer of claim 1.

16. A method of preventing fouling in an industrial process stream, the method comprising adding 0.1 ppm to 10,000 ppm of a polymer of claim 1 to the industrial process stream.

17. The method of claim 16 wherein the industrial process stream is a crude oil.

18. The method of claim 16 wherein the industrial process stream comprises one or more polymerizable species.

19. A treated industrial process stream comprising
the polymer of claim 1; and
an industrial process stream comprising a foulant.

20. The treated industrial process stream of claim 19 wherein the foulant comprises an asphaltene or a wax.

21. An industrial process system comprising the treated industrial process stream of claim 19 disposed within the system and in fluid contact with a surface therein.

* * * * *